United States Patent
Hill

(10) Patent No.: US 7,328,711 B2
(45) Date of Patent: Feb. 12, 2008

(54) ORTHODONTIC FLOSSING IMPLEMENT AND METHOD OF USE THEREOF

(76) Inventor: Anthony Jason Hill, 500 Gale Ct., Alpharetta, GA (US) 30004

( * ) Notice: Subject to any disclaimer, the term of this patent is extended or adjusted under 35 U.S.C. 154(b) by 220 days.

(21) Appl. No.: 11/114,694

(22) Filed: Apr. 26, 2005

(65) Prior Publication Data

US 2005/0241665 A1    Nov. 3, 2005

Related U.S. Application Data

(60) Provisional application No. 60/566,376, filed on Apr. 30, 2004.

(51) Int. Cl.
*A61C 15/00* (2006.01)
(52) U.S. Cl. ...................................... 132/323
(58) Field of Classification Search ......... 132/321–329
See application file for complete search history.

(56) References Cited

U.S. PATENT DOCUMENTS

| | | | |
|---|---|---|---|
| 2,517,806 A * | 8/1950 | Streiler ........................ | 132/309 |
| 4,597,398 A * | 7/1986 | Chu ............................ | 132/324 |
| 5,050,625 A * | 9/1991 | Siekmann .................... | 132/323 |
| 5,101,843 A * | 4/1992 | Peng ........................... | 132/323 |
| 5,184,631 A * | 2/1993 | Ikeda .......................... | 132/323 |
| 5,638,841 A | 6/1997 | Levine | |
| 5,735,299 A * | 4/1998 | Kaltenbach .................. | 132/323 |
| 5,860,434 A * | 1/1999 | Sines et al. .................. | 132/323 |
| 5,899,214 A * | 5/1999 | Francis ....................... | 132/323 |
| 5,904,153 A | 5/1999 | Meibauer | |
| 2003/0150474 A1* | 8/2003 | Doyscher .................... | 132/325 |
| 2004/0003827 A1* | 1/2004 | Gwen ......................... | 132/323 |
| 2004/0154636 A1* | 8/2004 | Paz-Soldan ................. | 132/323 |

* cited by examiner

*Primary Examiner*—Todd E. Manahan
*Assistant Examiner*—Rachel A. Running
(74) *Attorney, Agent, or Firm*—Myers & Kaplan, LLC; Ash D. Patel; George P. Bonanto

(57) ABSTRACT

An orthodontic flossing implement and method of use thereof, wherein the present implement comprises a handle from which extends a flat, narrow arm, and wherein the tip of the arm comprises a slit or aperture through which a desired length of floss is inserted. The narrow arm, with the length of floss threaded therethrough, may be quickly and simply inserted underneath a selected arch or pass of a brace wire, wherein the length of floss hanging from the arm aperture may then be easily grasped and worked within and along the inter-dental space disposed proximate or behind the selected wire arch. Thereafter, the arm of the flossing implement is retracted and systematically moved between each arch of the wire, whilst maintaining the floss through the aperture of the arm, whereupon each respective underlying inter-dental space may be conveniently and quickly flossed.

4 Claims, 6 Drawing Sheets

ORTHODONTIC FLOSSING IMPLEMENT AND METHOD OF USE THEREOF

CROSS-REFERENCE AND PRIORITY CLAIM TO RELATED APPLICATIONS

To the fullest extent permitted by law, the present non-provisional patent application claims priority to and the full benefit of provisional patent application entitled "Floss Pick (Ortho Flossing Tool)", filed on Apr. 30, 2004, and having assigned Ser. No. 60/566,376.

TECHNICAL FIELD

The present invention relates generally to dental hygiene devices, and more specifically to an orthodontic flossing implement and method of use thereof, wherein the present invention facilitates inter-dental flossing of orthodontically-treated teeth and, in particular, teeth fitted with braces.

BACKGROUND OF THE INVENTION

Flossing is essential to proper daily oral hygiene, as it functions to effectively remove bacterial plaque between teeth and at the gum line—areas generally inaccessible through conventional brushing techniques. Indeed, regular flossing is often the first defense to the prevention or onset of periodontal disease and/or gingivitis. Although a multitude of flossing instruments are currently available to facilitate such regular dental practice, dental floss or flossing thread remains the most convenient and popular choice amongst the general populace, and often the most highly-recommended by dental practitioners.

Unfortunately, individuals with orthodontically-treated teeth and, in particular, those individuals with braces, experience significant difficulties in maneuvering dental floss between the brace structures to access the teeth and gum line structures. Specifically, with conventional fixed brace systems spanning the upper and/or lower rows of teeth, the front surface of each tooth comprises a bracket cemented or otherwise affixed thereto, wherein a wire ("archwire") extends between and through each bracket. As such, in the fixed brace configuration, the wire interrupts or prevents full passage of the dental floss between each tooth; thus, hindering effective inter-dental flossing.

In an attempt to circumvent the structural obstacles imposed by such fixed brace assemblies, many brace-adorned individuals will often utilize inter-proximal brushes and/or oral irrigators (i.e., water picks) to get underneath or past the wire. However, inter-proximal brushes do not effectively access the gum line, and oral irrigators, usually utilized to remove inter-dental food particles, fail to provide the requisite "mechanical" interface needed to frictionally remove plaque deposits.

As an alternative to the foregoing dental products, many brace wearers utilize a floss threader to wedge or push dental floss underneath the wire. Unfortunately, the floss threader must be utilized to feed the dental floss between each arch or pass of the wire extending between each bracket of each tooth to access each inter-dental space; thus, significantly increasing overall flossing time. Indeed, with such floss threaders, the user must often utilize his/her thumb and index finger in an attempt to grab or pinch the floss fed underneath the wire, and then, after laying the floss threader down, coil the strand of dental floss around his/her "flossing fingers", and resume flossing—a series of steps that must be repeated for each inter-dental space of each tooth within the upper and lower brace-fitted rows of teeth.

Therefore, it is readily apparent that there is a need for an orthodontic flossing implement and method of use thereof, wherein the present invention facilitates the effective and expeditious flossing between brace-fitted teeth, and along the gum line, by enabling the individual to simply insert the present pre-threaded flossing implement underneath each arch of the wire, floss between an inter-dental space, and subsequently retract the flossing implement, whilst maintaining the floss with the flossing implement; thus, enabling the user to systematically move between each arch of the wire and floss the inter-dental space proximate thereto, without having to re-thread floss between each arch or pass of the wire.

BRIEF SUMMARY OF THE INVENTION

Briefly described, in a preferred embodiment, the present invention overcomes the above-mentioned disadvantage, and meets the recognized need for such an invention by providing an orthodontic flossing implement and method of use thereof, wherein the present implement comprises a handle from which extends a flat, narrow arm, and wherein the tip of the arm comprises a slit or aperture through which a desired length of floss is inserted. The narrow arm, with the length of floss threaded therethrough, may be quickly and simply inserted underneath a selected arch or pass of a brace wire, wherein the length of floss hanging from the arm aperture may then be easily grasped and worked within and along the inter-dental space disposed proximate or behind the selected wire arch. Thereafter, the arm of the flossing implement is retracted and systematically moved between each arch of the wire, whilst maintaining the floss through the aperture of the arm, whereupon each respective underlying inter-dental space may be conveniently and quickly flossed.

According to its major aspects and broadly stated, the present invention in its preferred form is an orthodontic flossing implement and method of use thereof, comprising a handle, an arm extending from the handle, and an aperture formed through the arm for receiving floss therethrough.

More specifically, the present invention is an orthodontic flossing implement and method of use thereof, comprising a handle over which dental floss may be conveniently wrapped and stored. Preferably extending from the handle is an arm dimensioned for introduction underneath the wire of a conventional fixed brace assembly. An aperture formed through the tip of the arm preferably functions to receive a length of dental floss therethrough.

In use, the arm of the flossing implement, with the length of floss threaded therethrough, is inserted underneath a selected arch of the brace wire; thereby, positioning the arm's aperture, and a portion of the length of floss extending therethrough, over a particular inter-dental space. As such, the length of floss may be brought behind the user's teeth and into the inter-dental space, where the floss may be worked therewithin. Thereafter, the arm of the flossing implement is retracted and systematically moved between each arch of the wire, whilst maintaining the floss through the aperture of the arm, whereupon each respective underlying inter-dental space may be conveniently and quickly flossed.

Accordingly, a feature and advantage of the present invention is its ability to provide an orthodontic flossing implement that facilitates effective and expeditious flossing between brace-fitted teeth, as well as and along the gum line.

Another feature and advantage of the present invention is its ability to provide an orthodontic flossing implement that maintains the floss within the flossing implement during use; thus, avoiding re-threading of the floss between each arch or pass of the wire, as is required with conventional flossing threaders.

Still another feature and advantage of the present invention is its ability to provide a flossing implement that facilitates inter-dental flossing of orthodontically-treated teeth, in general.

Yet another feature and advantage of the present invention is its ability to be manufactured as a disposable, one-time use product; thereby, promoting hygienic flossing practice.

These and other features and advantages of the invention will become more apparent to one skilled in the art from the following description and claims when read in light of the accompanying drawings.

BRIEF DESCRIPTION OF THE DRAWINGS

The present invention will be better understood by reading the Detailed Description of the Preferred and Alternate Embodiments with reference to the accompanying drawing figures, in which like reference numerals denote similar structure and refer to like elements throughout, and in which:

FIG. 3A is a partial perspective view of an orthodontic flossing implement according to a preferred embodiment of the present invention, showing dental floss cooperatively engaged therewith and in use;

DETAILED DESCRIPTION OF THE PREFERRED AND ALTERNATIVE EMBODIMENTS

In describing the preferred and alternate embodiments of the present invention, as illustrated in FIGS. 1-6, specific terminology is employed for the sake of clarity. The invention, however, is not intended to be limited to the specific terminology so selected, and it is to be understood that each specific element includes all technical equivalents that operate in a similar manner to accomplish similar functions.

Referring now to FIGS. 1-3A, the present invention in its preferred embodiment is an orthodontic flossing implement 10 and method of use thereof, wherein flossing implement 10 preferably comprises handle portion 20, from which extends arm 40 integrally formed therewith. Flossing implement 10 is preferably formed from a suitable plastic substrate and manufactured with sufficient rigidity to withstand application within the present method of use.

Figure 1:
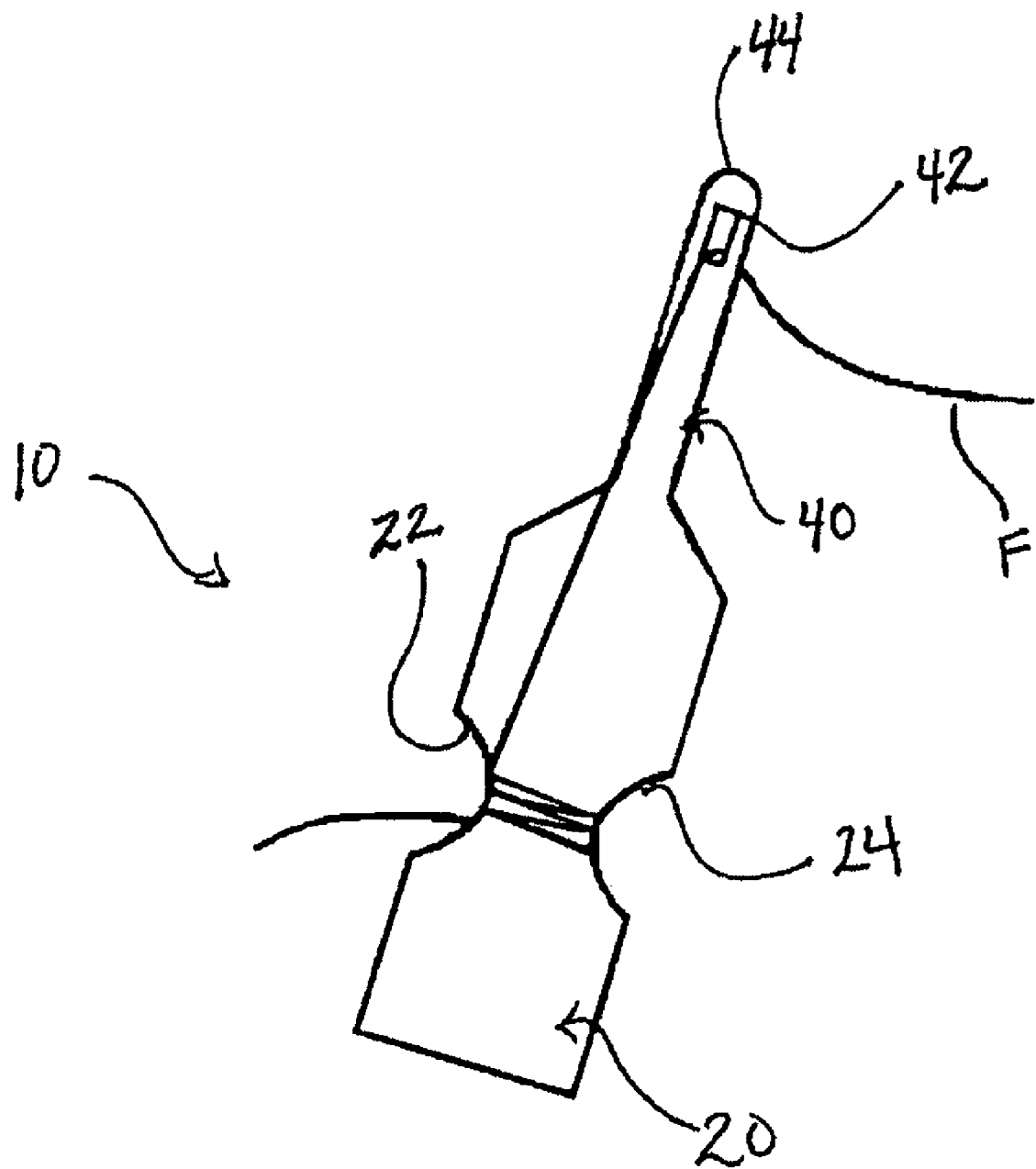
FIG. 1 is a perspective view of an orthodontic flossing implement according to a preferred embodiment of the present invention, showing dental floss cooperatively engaged therewith.

Specifically, handle 20 is substantially flat and is grasped by the user during use of flossing implement 10. Handle 20 preferably comprises opposing grooves 22, 24 disposed proximate the mid-region thereof, over which dental floss may be conveniently wrapped and stored, as is best illustrated in FIG. 1. It is contemplated that handle 20 may comprises a textured, ribbed, rubberized or other frictional surface to facilitate secure grasping of handle 20 during use of flossing implement 10.

Preferably extending from handle 20 is flat, narrow arm 40, wherein arm 40 preferably comprises a dimension suitable for unhindered access underneath each pass of archwire W of conventional fixed brace assembly B, as more fully described below. For exemplary purposes only, it is contemplated that arm 40 may comprise a width of approximately 1/16 inch, a length of approximately 3/4 inch, and a thickness of approximately 1/32 inch; however, it should be recognized that arm 40 may be manufactured to any selected dimension which would otherwise facilitate insertion of arm 40 underneath wire W of brace assembly B, or any other corrective orthodontic assembly (i.e., a thickness less than the spatial gap or distance between arch A of wire W and inter-dental space S proximate thereto).

Preferably formed through tip 44 of arm 40 is aperture 42, wherein aperture 42 preferably functions to receive a length of dental floss F therethrough, wherein length of dental floss F is preferably utilized to access inter-dental space S between the user's teeth T, as well as the associated gum line G.

Figure 2:
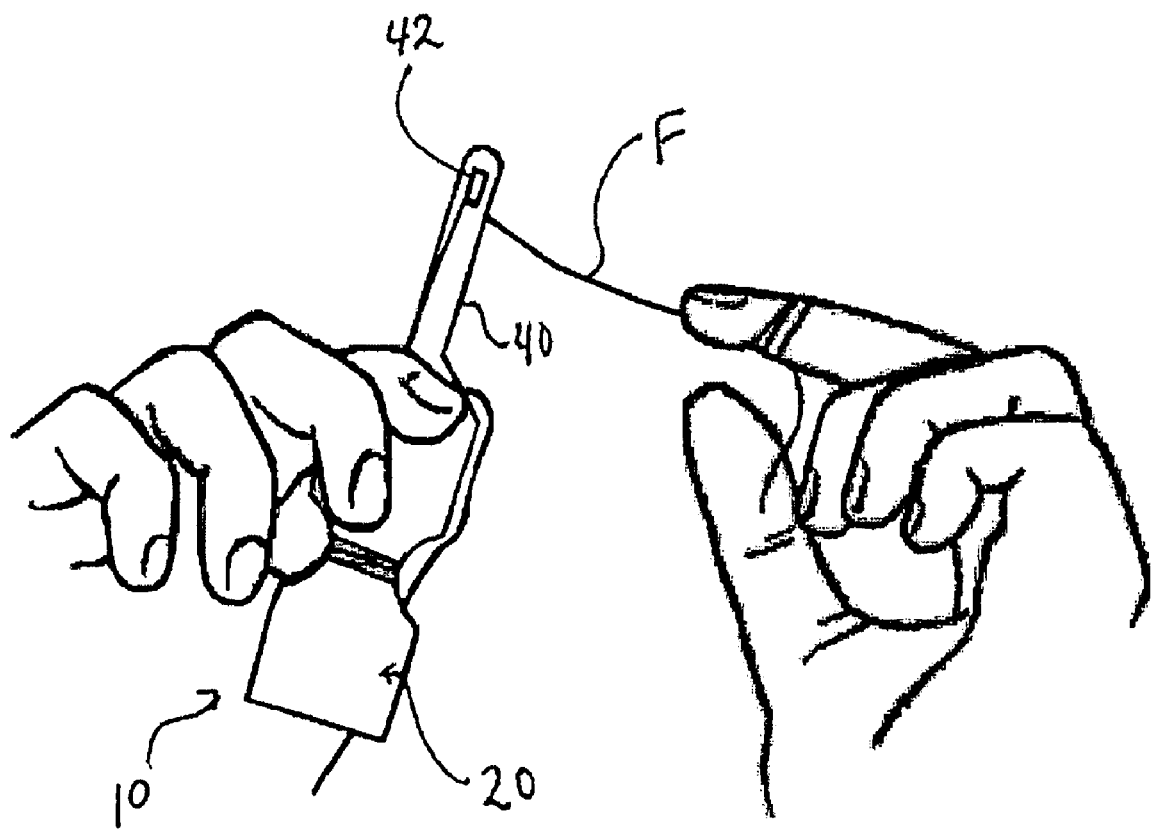
FIG. 2 is a perspective view of an orthodontic flossing implement according to a preferred embodiment of the present invention, showing dental floss cooperatively engaged therewith and in use.
Figure 3:
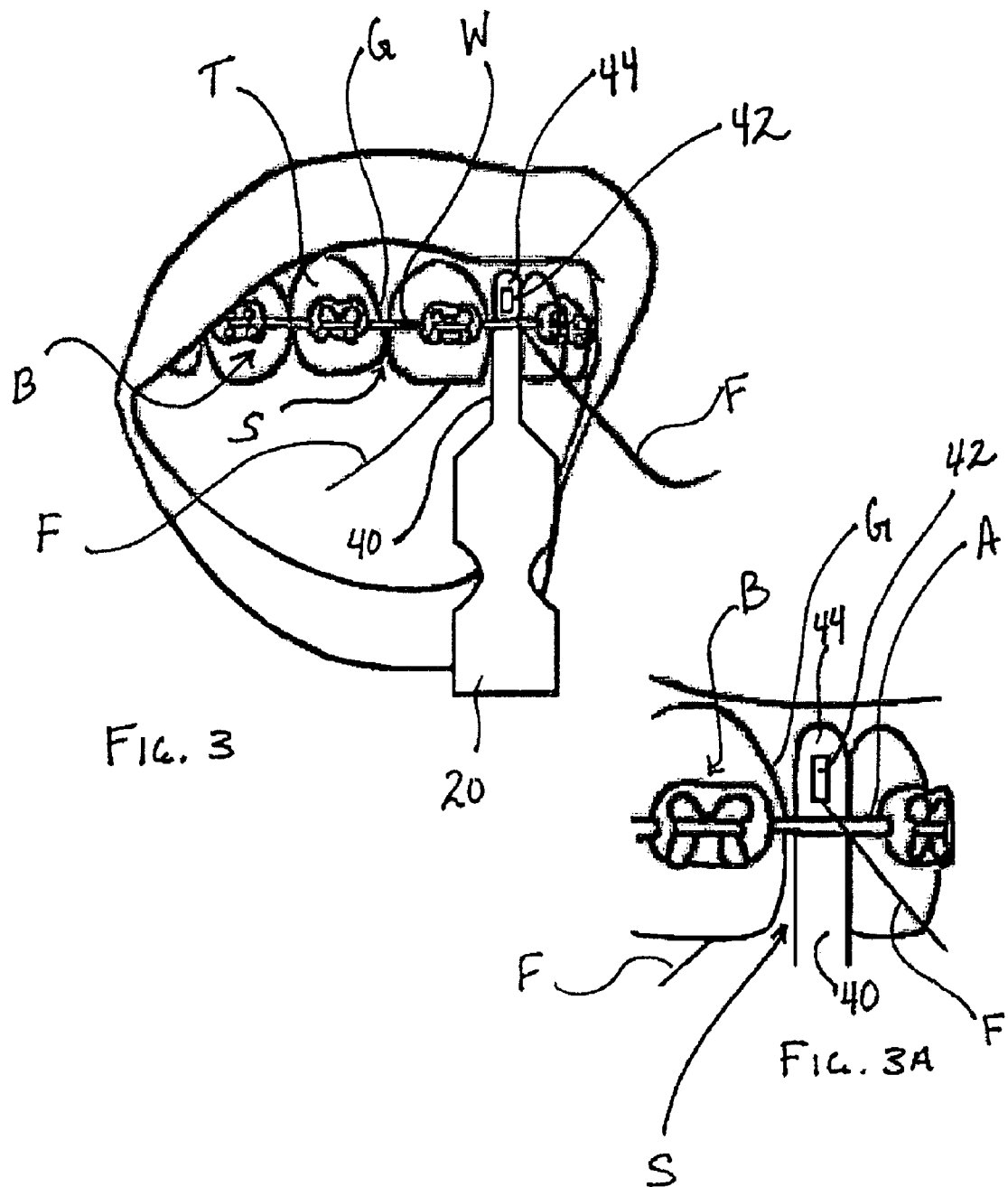
FIG. 3 is a perspective view of an orthodontic flossing implement according to a preferred embodiment of the present invention, showing dental floss cooperatively engaged therewith and in use.

Referring now more specifically to FIGS. 3-3A, in use, tip 44 of narrow arm 40, with length of floss F threaded through aperture 42, is preferably inserted underneath a selected pass or arch A of brace wire W, wherein length of floss F may be an independent strand of floss, or a length of floss unraveled and extending from the dental floss wrapped around grooves 22, 24 of handle 20 (see FIG. 2). When tip 44 of arm 40 is inserted underneath arch A of wire W, aperture 42 of arm 40 is positioned or disposed over an inter-dental space S, as is length of floss F extending from aperture 42. Accordingly, length of floss F hanging from aperture 42 is simply grasped and brought behind user's teeth T and into inter-dental space S, where floss F is worked therewithin in either a conventional manner (i.e., coiling opposing ends of the floss strand around flossing fingers) or, if length of floss F extends from the dental floss wrapped around handle 20, then by coiling length of floss F (disposed within the mouth) around one finger, and grasping handle 20 so as to tighten length of floss F for effective introduction into gum line G, and inter-dental space S generally. Alternatively, length of floss F may be coiled around the flossing finger prior to insertion of tip 44 of arm 40 underneath selected arch A of wire W.

Thereafter, the arm of the flossing implement is retracted and systematically moved between each arch A of wire W, whilst maintaining the floss through aperture 42 of arm 40, whereupon each respective underlying inter-dental space S may be conveniently and quickly flossed as described hereinabove. Notably, because flossing implement 10 maintains floss F within aperture 42 of arm 40 during use, re-threading of floss F between each arch A or pass of wire W may be conveniently avoided. Such a feature of present invention provides a distinct advantage over conventional flossing threaders.

Figure 4:
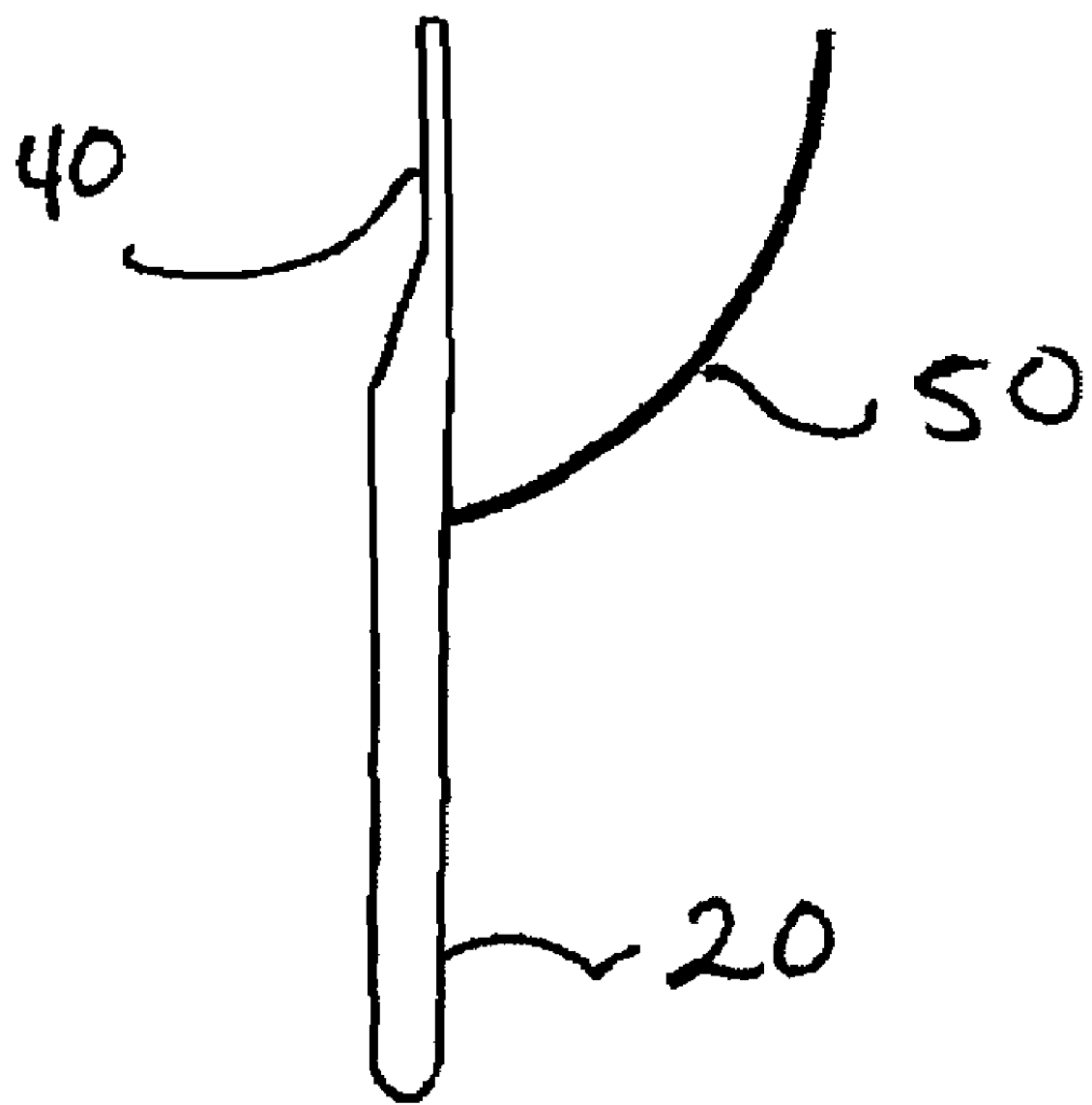
FIG. 4 is a side view of an orthodontic flossing implement according to an alternate embodiment of the present invention.
Figure 5:
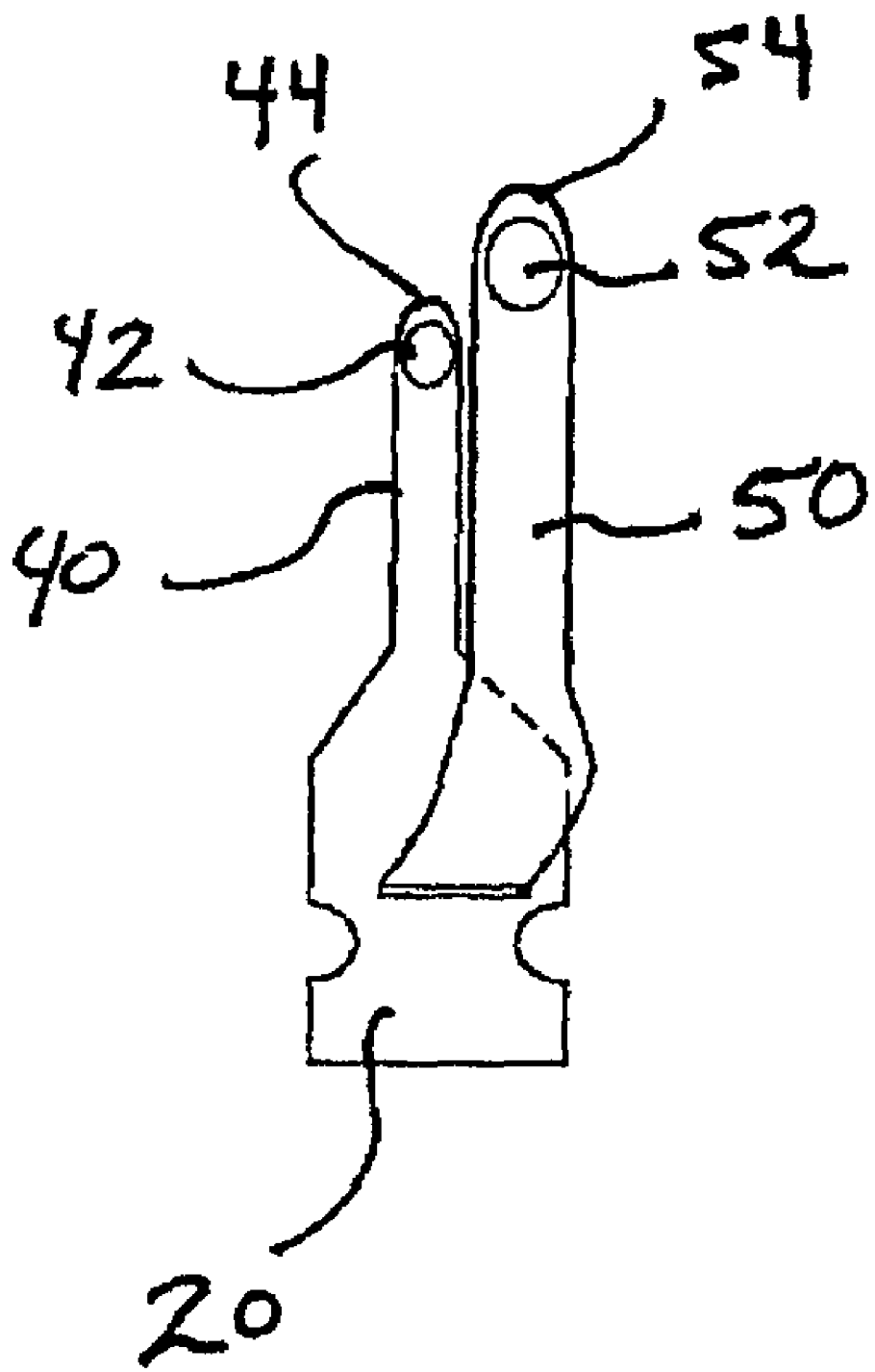
FIG. 5 is a perspective view of an orthodontic flossing implement according to the alternate embodiment of FIG. 4; and, FIG. 6 is a front view of an orthodontic flossing implement according to an alternate embodiment of the present invention.

Referring now more specifically to FIGS. 4-5, illustrated therein is an alternate embodiment of flossing implement 10, wherein the alternate embodiment of FIGS. 4-5 is substantially equivalent in form and function to that of the preferred embodiment detailed and illustrated in FIGS. 1-3A except as hereinafter specifically referenced. Specifically, the embodiment of FIGS. 4-5 incorporates a rear floss support arm 50 extending from handle 20, proximate to arm 40. Similar to arm 40, an aperture 52 is formed though tip 54 of rear arm 50. In use, length of floss F (extending from the dental floss generally wrapped around handle 20) is threaded through aperture 42 of arm 40, and thereafter threaded through aperture 52 of rear arm 50. Accordingly, tip 44 of arm 40 is inserted into any selected arch A of wire w, as described above, wherein rear arm 50 is positioned within the user's mouth and behind his/her teeth T, and wherein length of floss F and handle 20 are grasped so as to tighten length of floss F extending between apertures 42, 52 of arms 40, 50, respectively; thereby, enabling effective introduction of floss F into gum line G, and inter-dental space S generally.

Figure 6:
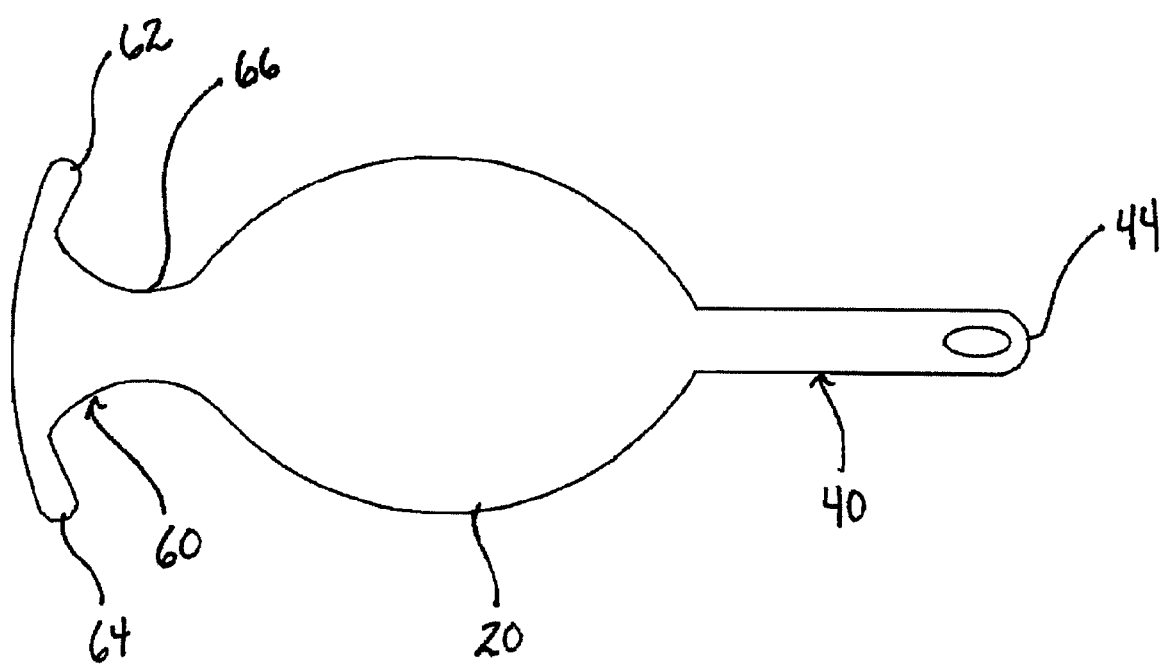

Referring now more specifically to FIG. 6, illustrated therein is an alternate embodiment of flossing implement 10, wherein the alternate embodiment of FIG. 6 is substantially equivalent in form and function to that of the preferred embodiment detailed and illustrated in FIGS. 1-3A except as hereinafter specifically referenced. Specifically, the embodiment of FIG. 6 incorporates food dislodger 60, disposed opposite tip 44 of arm 40 of flossing implement 10. Dislodger 60 comprises opposingly-disposed hook-shaped members 62, 64, wherein hook-shaped members 62, 64 comprises a dimension and thickness substantially similar to that of tip 44 of arm 40 (i.e., a thickness less than the spatial gap or distance between arch A of wire W and inter-dental space S proximate thereto); thereby, facilitating insertion of hook-shaped members 62, 64 underneath wire W of brace assembly B, or any other corrective orthodontic assembly, for dislodging and removing food particles therefrom. The instant alternate embodiment further comprises neck portion 66, disposed proximate dislodger 60, wherein neck portion 66 may receive dental floss wrapped therearound. Additionally, handle 20 of the instant alternate embodiment is substantially oval-shaped so as to facilitate comfortable gripping of same, wherein handle 20 may further comprise a textured, ribbed, rubberized or other frictional surface to further facilitate secure grasping of handle 20 during use of flossing implement 10.

It is contemplated in an alternate embodiment that flossing implement 10 may include a spool of floss integrally formed therewith, or otherwise affixed to and carried thereby, so as to facilitate dispensing of floss F.

It is contemplated in another alternate embodiment that flossing implement 10 may be manufactured as a reusable or disposable tool.

It is contemplated in still another alternate embodiment that flossing implement 10 may be manufactured with a pick integrally formed therewith.

It is contemplated in yet another alternate embodiment that arm 40 may be disposed at any angle relative to handle 20, as opposed to being disposed coplanar with handle 20.

Having thus described exemplary embodiments of the present invention, it should be noted by those skilled in the art that the within disclosures are exemplary only, and that various other alternatives, adaptations, and modifications may be made within the scope of the present invention. Accordingly, the present invention is not limited to the specific embodiments illustrated herein, but is limited only by the following claims.

What is claimed is:

1. An orthodontic flossing implement for accessing an inter-dental space proximate an arch of a brace wire, said orthodontic flossing implement comprising:
   an arm;
   a handle, wherein said arm is integrally formed with said handle and disposed coplanar therewith, and wherein said arm is flat and dimensionally narrower than said handle;
   at least one projection, said projection separated from said handle by a neck; and, an aperture formed transversely through a tip of said arm, wherein said aperture is adapted to receive floss threaded therethrough, wherein said neck comprises a dimensionally narrower section, said neck adapted to retain dental floss wrapped therearound,
   wherein said tip of said arm is inserted underneath the arch of the brace wire so as to position said aperture, and at least a portion of the floss carried thereby, over the inter-dental space disposed proximate the arch of the brace wire.

2. The flossing implement of claim 1, wherein said neck comprises a first and a second opposing groove.

3. The flossing implement of claim 1, wherein said arm comprises a thickness less than the spatial gap or distance between the arch of the wire and the inter-dental space proximate to the arch.

4. The flossing implement of claim 1, wherein said at least one projection comprises a food dislodger, said food dislodger comprising a hook-shaped member that may be inserted underneath the arch of the brace wire for dislodging and removing food particles therefrom.

* * * * *